(12) United States Patent
Aoki et al.

(10) Patent No.: US 10,624,201 B2
(45) Date of Patent: Apr. 14, 2020

(54) CIRCULAR ACCELERATOR

(71) Applicant: HITACHI, LTD., Tokyo (JP)

(72) Inventors: Takamichi Aoki, Tokyo (JP); Fuutarou Ebina, Tokyo (JP); Yuto Nakashima, Tokyo (JP)

(73) Assignee: Hitachi, Ltd., Tokyo (JP)

(*) Notice: Subject to any disclaimer, the term of this patent is extended or adjusted under 35 U.S.C. 154(b) by 0 days.

(21) Appl. No.: 16/341,077

(22) PCT Filed: Feb. 1, 2017

(86) PCT No.: PCT/JP2017/003508
§ 371 (c)(1),
(2) Date: Apr. 11, 2019

(87) PCT Pub. No.: WO2018/142495
PCT Pub. Date: Aug. 9, 2018

(65) Prior Publication Data
US 2019/0239334 A1 Aug. 1, 2019

(51) Int. Cl.
*H05H 7/04* (2006.01)
*H01F 7/20* (2006.01)
(Continued)

(52) U.S. Cl.
CPC .............. *H05H 7/04* (2013.01); *H01F 7/202* (2013.01); *H05H 13/005* (2013.01);
(Continued)

(58) Field of Classification Search
None
See application file for complete search history.

(56) References Cited

U.S. PATENT DOCUMENTS 8,374,306 B2 * 2/2013 Norling .................... G21G 1/10
376/190
9,895,552 B2 * 2/2018 Antaya ..................... H01F 6/06
(Continued)

FOREIGN PATENT DOCUMENTS

JP      58-179800 U    12/1983
JP      02-69500 U     5/1990
(Continued)

OTHER PUBLICATIONS

International Search Report of PCT/JP2017/003508 dated May 9, 2017.

*Primary Examiner* — Alexander H Taningco
*Assistant Examiner* — Srinivas Sathiraju
(74) *Attorney, Agent, or Firm* — Mattingly & Malur, PC

(57) ABSTRACT

Conventional cyclotrons have been incapable of changing energy of a beam to be extracted. Conventional synchrotrons have been difficult to output beams in a continuous manner. An accelerator has a dense region dense region in which orbits of different energies densely gather as a result of using a radiofrequency electric field to accelerate an ion orbiting in an isochronous magnetic field in order to cause a beam orbit to be displaced in a specific direction with increasing acceleration, and a sparse region in which orbits of different energies are sparsely discrete from each other. The accelerator has a feature that a magnetic field has a magnetic field gradient in a radial direction of a beam orbit in the dense region, and a product of a gradient of magnetic field gradient and a beam size passing through the dense region becomes smaller than the magnetic field gradient.

6 Claims, 12 Drawing Sheets

(51) Int. Cl.
*H05H 13/00* (2006.01)
*H05H 13/02* (2006.01)
*H05H 15/00* (2006.01)
*A61N 5/10* (2006.01)

(52) U.S. Cl.
CPC ............ *H05H 13/02* (2013.01); *H05H 15/00* (2013.01); *A61N 5/1077* (2013.01); *A61N 2005/1087* (2013.01)

(56) References Cited

U.S. PATENT DOCUMENTS

| 10,306,745 | B2* | 5/2019 | Aoki | A61N 5/10 |
| 2006/0164026 | A1* | 7/2006 | Sasaki | H05H 13/00 |
| | | | | 315/502 |
| 2011/0291484 | A1* | 12/2011 | Tsutsui | H05H 7/08 |
| | | | | 307/66 |
| 2011/0298397 | A1* | 12/2011 | Campbell | G02B 6/02357 |
| | | | | 315/501 |
| 2013/0009571 | A1* | 1/2013 | Antaya | H05H 13/005 |
| | | | | 315/502 |
| 2013/0249443 | A1* | 9/2013 | Antaya | H05H 7/10 |
| | | | | 315/502 |
| 2014/0014851 | A1* | 1/2014 | Asaba | H01J 3/08 |
| | | | | 250/396 R |
| 2014/0062343 | A1* | 3/2014 | Miyashita | H05H 7/00 |
| | | | | 315/502 |
| 2015/0084548 | A1* | 3/2015 | Hara | H05H 13/005 |
| | | | | 315/501 |
| 2016/0143124 | A1* | 5/2016 | Kleeven | H05H 13/005 |
| | | | | 315/502 |
| 2016/0353562 | A1* | 12/2016 | Antaya | H01F 6/06 |
| 2016/0381780 | A1* | 12/2016 | Subotic | H05H 7/04 |
| | | | | 313/62 |
| 2017/0303384 | A1* | 10/2017 | Aoki | H05H 7/08 |
| 2017/0318657 | A1* | 11/2017 | Aoki | A61N 5/10 |
| 2017/0332474 | A1* | 11/2017 | Abs | H05H 7/04 |
| 2017/0332475 | A1* | 11/2017 | Kleeven | H05H 7/04 |
| 2017/0339778 | A1* | 11/2017 | Aoki | A61N 5/1077 |
| 2019/0239333 | A1* | 8/2019 | Aoki | H05H 7/04 |
| 2019/0239334 | A1* | 8/2019 | Aoki | H05H 7/04 |

FOREIGN PATENT DOCUMENTS

| JP | 06-132098 A | 5/1994 |
| JP | 2011-249118 A | 12/2011 |
| JP | 2014-020800 A | 2/2014 |
| JP | 2014-160613 A | 9/2014 |
| JP | 2014-186939 A | 10/2014 |
| WO | 2016/092621 A1 | 6/2016 |
| WO | 2016/092622 A1 | 6/2016 |

* cited by examiner

CIRCULAR ACCELERATOR

TECHNICAL FIELD

The present invention relates to an accelerator that accelerates protons or heavy ions such as carbon ions or the like.

BACKGROUND ART

High-energy nuclear beams used in particle therapy, physical experiments and the like are produced using an accelerator. Examples of an accelerator to provide beams with kinetic energy of around 200 MeV per nucleon include a cyclotron disclosed in Patent Literature 1 and Patent Literature 2, a synchrotron disclosed in Patent Literature 3 and a variable energy accelerator disclosed in Patent Literature 4. A feature of the cyclotron is that a beam orbiting in a static magnet field is accelerated with a radiofrequency electric field, in which with increasing acceleration, the beam increases a curvature radius of its orbit, then moves to an outer orbit, and then reaching the highest energy, followed by beam extraction. Because of this, the energy of the extracted beam is fixed. The synchrotron varies, with time, the magnetic field of an electromagnet for bending the beam and the frequency of the radiofrequency electric field for acceleration in order for the beam to move in a certain orbit. Therefore, the beam is able to be extracted before the design maximum energy is reached, and also the energy to be extracted is controllable. The variable energy accelerator has a feature that, as in the case of the cyclotron, while the beam orbiting in the magnetic field is accelerated with a radiofrequency electric field, the beam orbit becomes more eccentric in one direction with increasing acceleration.

CITATION LIST

Patent Literature

Patent Literature 1: Japanese Unexamined Patent Application Publication No. 2014-160613
Patent Literature 2: Japanese Unexamined Patent Application Publication No. 2014-020800
Patent Literature 3: Japanese Unexamined Patent Application Publication No. 2014-186939
Patent Literature 4: WO 2016-092621

SUMMARY OF INVENTION

Technical Problem

In the variable energy accelerator disclosed in Patent Literature 4, from the characteristics of an orbit becoming more eccentric in one direction with increasing acceleration, there exist two regions, a region in which orbits of the respective energies approach each other, resulting in being densely located (dense region), and a region in which orbits of the respective energies distance from each other (sparse region). On the other hand, similarly to the cyclotron, the variable energy accelerator requires an isochronous magnetic field in which the orbit time is unchanged for energy. A feature of the isochronous magnetic field is that an average magnetic field on a beam orbit is proportional to a relativistic factor $\gamma$ of the beam. Therefore, in general, in comparison between the magnetic field on a high-energy beam orbit and the magnetic field on a low-energy beam orbit, the magnet field in the high-energy beam orbit is lager. Then, a second derivative of a magnetic field along two in-plane directions vertical to the beam orbit (gradient of magnetic field gradient) occurs, resulting in disturbance to a convergent force supporting stable orbital movement of the beam. Accordingly, in order to ensure the amount of orbiting beams in the variable energy accelerator, based on consideration given to the gradient of magnetic field gradient, a need exists to define an on-orbit magnetic field. However, no guiding principle for this has conventionally been issued.

Solution to Problem

To attain the above object, an aspect of the present invention provides an accelerator that has a dense region dense region in which orbits of different energies densely gather as a result of using a radiofrequency electric field to accelerate an ion orbiting in an isochronous magnetic field in order to cause a beam orbit to be displaced in a specific direction with increasing acceleration, and a sparse region in which orbits of different energies are sparsely discrete from one another. The magnetic field has a magnetic field gradient in a radial direction of a beam orbit in the dense region, and a product of a gradient of magnetic field gradient and a beam size passing through the dense region becomes smaller than the magnetic field gradient.

Advantageous Effects of Invention

According to the present invention, an accelerator is capable of producing a larger amount of beams.

DESCRIPTION OF EMBODIMENTS

First Embodiment

Figure 1:
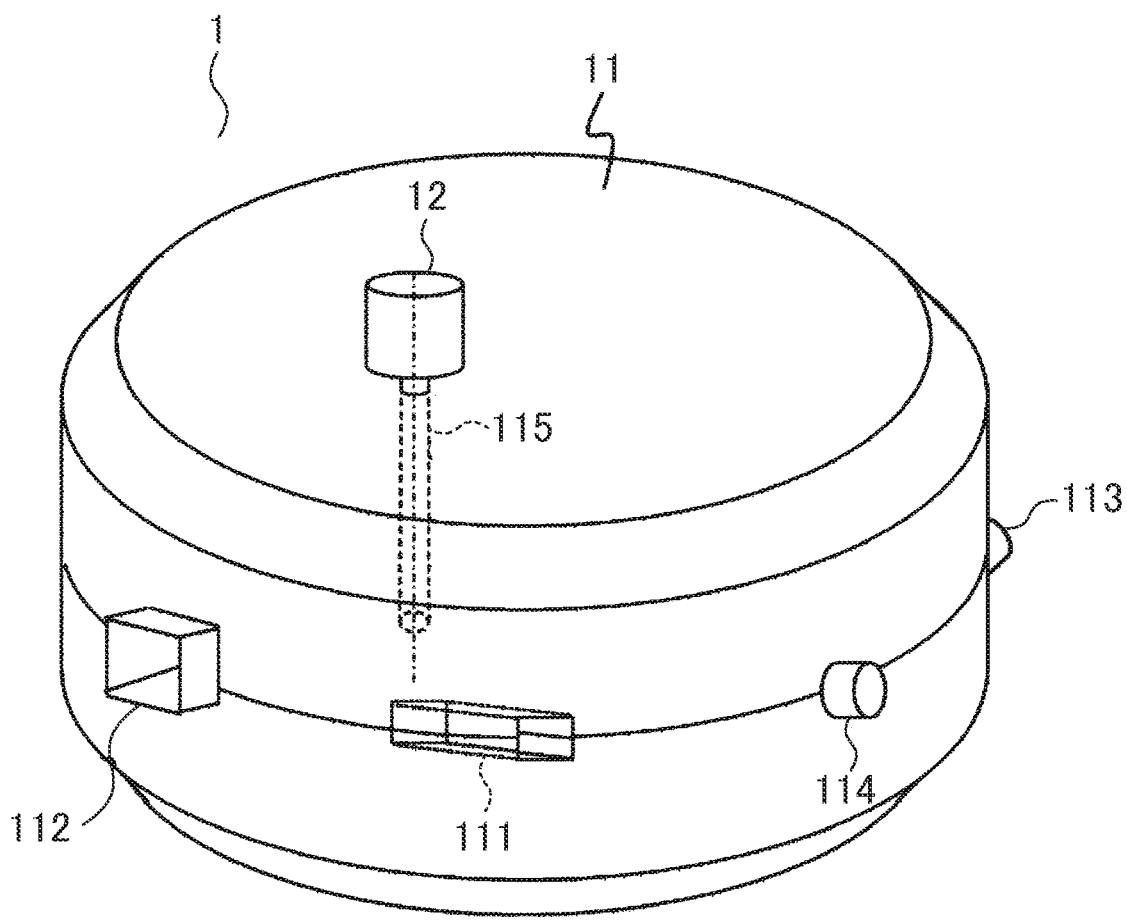
FIG. 1 is an overall schematic diagram of an accelerator 1 in accordance with the embodiment.

An accelerator in accordance with a first embodiment, which is a preferred embodiment according to the present invention, will now be described with reference to FIG. 1 to FIG. 12. The accelerator 1 in the embodiment is a variable energy accelerator capable of outputting a beam at different energies and in a continuous manner. The accelerator 1 is a circular accelerator that uses a radiofrequency electric field to accelerate an ion beam which orbits at a constant frequency in a constant magnetic field with respect to time (isochrony). The external appearance of the accelerator 1 is illustrated in FIG. 1. The accelerator 1 has an outer shell formed of vertically divisible magnet 11, and the interior thereof is evacuated. The magnet 11 has a plurality of through holes. Of the through holds, the beam extraction through hole 111 for extracting accelerated beam, pulling-out holes 112, 113 for pulling a coil out of the interior to outside, and a through hole 114 for incoming radiofrequency power are provided in a connection surface between the upper and lower magnets. An ion source 12 is also installed on a top of the magnet 11 so that beam is injected through a beam injection through hole 115 into the accelerator 1.

Figure 2:
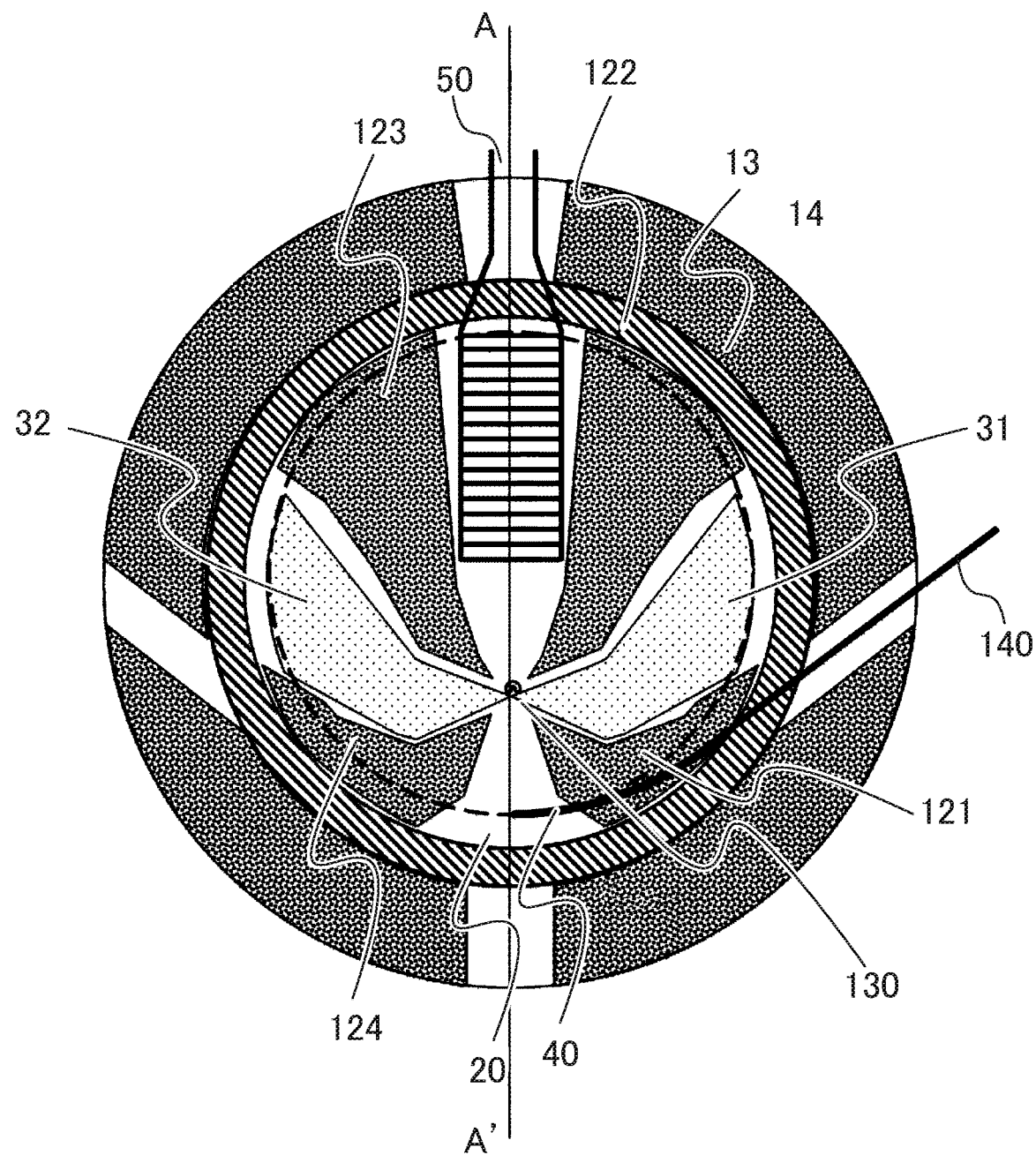
FIG. 2 is an internal structure of the accelerator 1 in accordance with the embodiment.

Next, the interior structure of the accelerator is described with reference to FIG. 2. In the interior of the magnet 11, a cylindrical empty space 20 is formed by a cylindrical inner wall, and an annular-shaped coil 13 is placed along the inner wall. The magnet 11 is magnetized by the passage of electric current through the coil 13, so that a magnetic field is excited in predetermined distribution in the interior of the magnet 11. Magnetic poles 121 to 124 are placed inside the coil 13, and a cylindrical return yoke 14 is installed on the outside of the coil 13. A beam orbits and accelerates within the interior space 20. The energy of extracted beam ranges from a minimum of 70 MeV to a maximum of 235 MeV, and the frequency of orbiting beam is 19.82 MHz.

The magnetic poles 121 to 124 form four sets of depressions and projections arranged along the beam orbit, and a magnetic field acting on the beam is a low magnetic field in the depression section, and is a high magnetic field in the projection section. In this manner, the magnetic field is varied in intensity along the beam orbit, and also an average value of the magnetic field along the orbit is proportional to a relativistic factor $\gamma$ of the beam. Thereby, the orbit time of the orbiting beam becomes constant independently of energy, while stable betatron oscillations occur with respect to a direction vertical to the orbit plane and orbit in-plane of beam. Installed in the magnetic-pole depression section are radiofrequency cavities 31, 32 that excite a radiofrequency electric field, a septum electromagnet 40 for extraction, and a coil 50 for generating a kicker magnetic field. As described later, for a kicker magnetic field, a massless septum scheme to apply a magnetic field only to a specified position is employed so that a magnetic field is excited by passing a current through the coil located symmetrically with respect to a beam in a direction vertical to the orbit plane.

The beam is injected from an injection point 130 into the accelerator 1 under conditions of low energy ions. Every time the injected beam passes through an electric filed gap, the beam is accelerated by the radiofrequency electric field excited by the radiofrequency cavity. In the accelerator 1, the beam orbit is defined such that the center of the beam orbit is moved in the same plane in one direction with increasing beam acceleration. Therefore, a magnetic pole shape and coil placement are designed to be mirror-symmetric with respect to the center plane such that the magnet field has an in-plane component becoming zero in the center plane. Also, the magnetic field distribution is left-right symmetric with respect to an axis AA' in the center plane. It follows that the magnetic poles 121 and 124, and the magnetic poles 122 and 123, each have a left-right symmetrical shape. A trim coil for fine adjustment of a magnetic field is placed in each magnetic pole, and the trim coil current is adjusted prior to operation in order to ensure isochronism and stable betatron oscillations.

Figure 3:
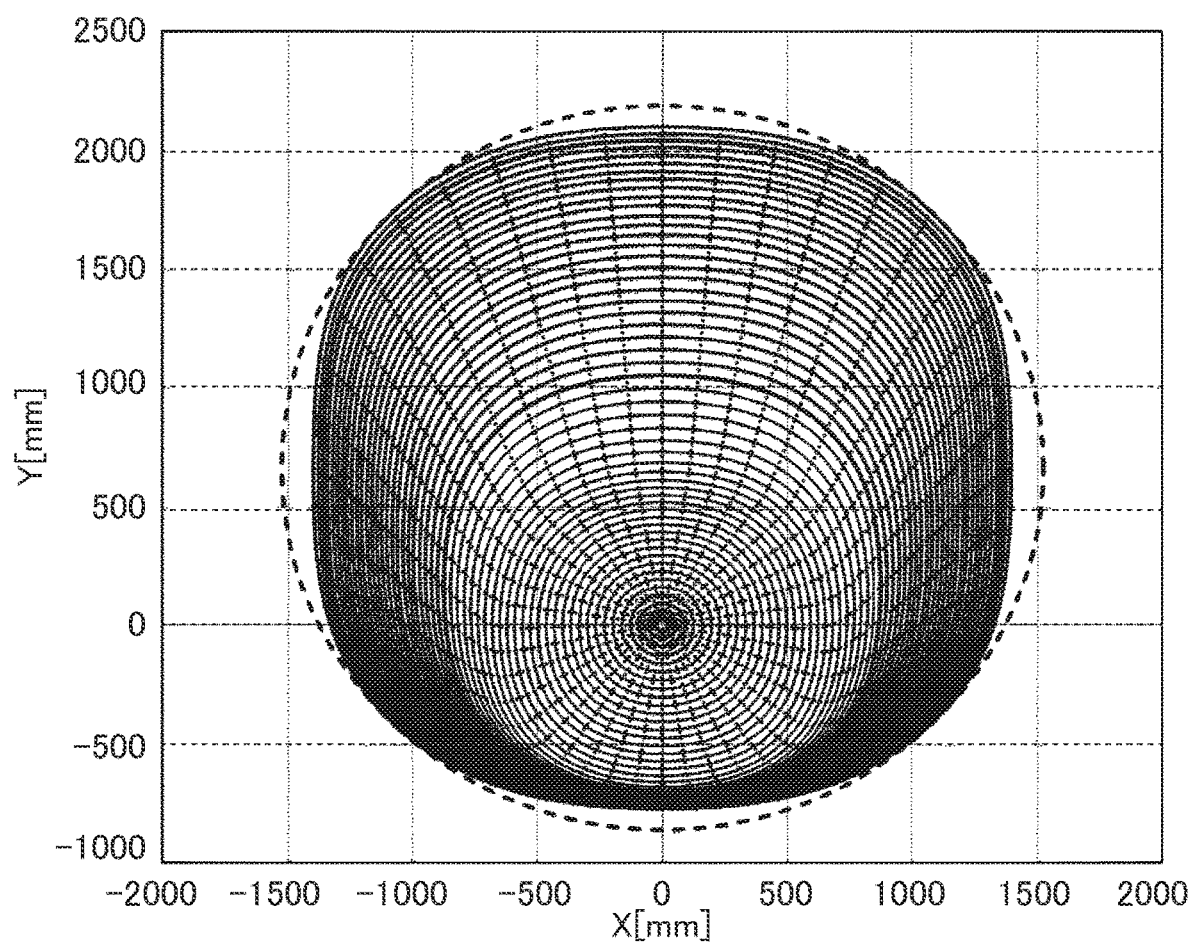
FIG. 3 shows design orbits in the accelerator 1 in accordance with the embodiment.

Next, the orbit of a beam orbiting in the accelerator is described. Each energy orbit is illustrated in FIG. 3. FIG. 3 represents graphically the orbit shape, assuming that the center plane is an X-Y plane. Regarding the closed orbit, a solid line shows a 50-energy orbit from the maximum energy 235 MeV on a magnetic rigidity 0.04 Tm basis. A dotted line indicates a line connecting the same orbital phases of each orbit, which is referred to as an "isochronous line". The isochronous line is plotted from the dense region on an orbital phase $\pi/20$ basis. Acceleration gaps are placed along the isochronous line. In the low energy region of 50 MeV or lower, the orbits are centered on around the ion injection point as in the case of the cyclotron. However, the energy orbits of higher than 50 MeV densely gather near the injection point of the septum electromagnet for extraction, whereas in the depression section with the massless septum 50 being installed, the orbits are positioned at a distance from each other. Assuming that the point where the orbits densely gather is referred to as the "dense region" and the region where the orbits are discrete is referred to as the "orbit sparse region". In the orbit sparse region, the beam spreads in a broad region in the center plane according to energy, and if an excitation position for the magnetic field by the massless septum is appropriately determined, the beam of energy corresponding to the excitation position are kicked. The beam, which has been displaced from a predetermined equilibrium orbit by the kick, is injected into the septum electromagnet placed in the dense region in a downstream half turn. The septum electromagnet gives to the beam deflection required for the extraction beam to be put into a design orbit defined on an extraction channel 140. Specifically, a magnetic field is excited in a direction of canceling a magnetic field of a main electromagnet, so that the beam is guided to the extraction channel 140.

Figure 4:
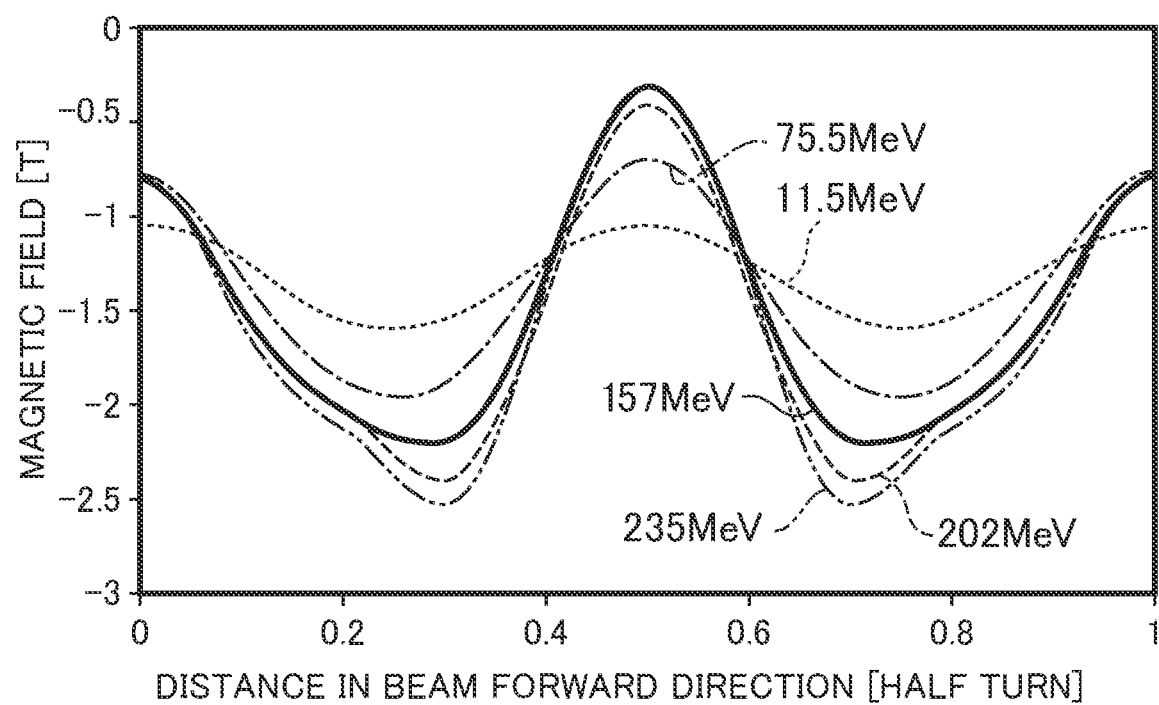
FIG. 4 is the magnetic field distribution along the beam orbit in the accelerator 1 in accordance with the embodiment.
Figure 5:
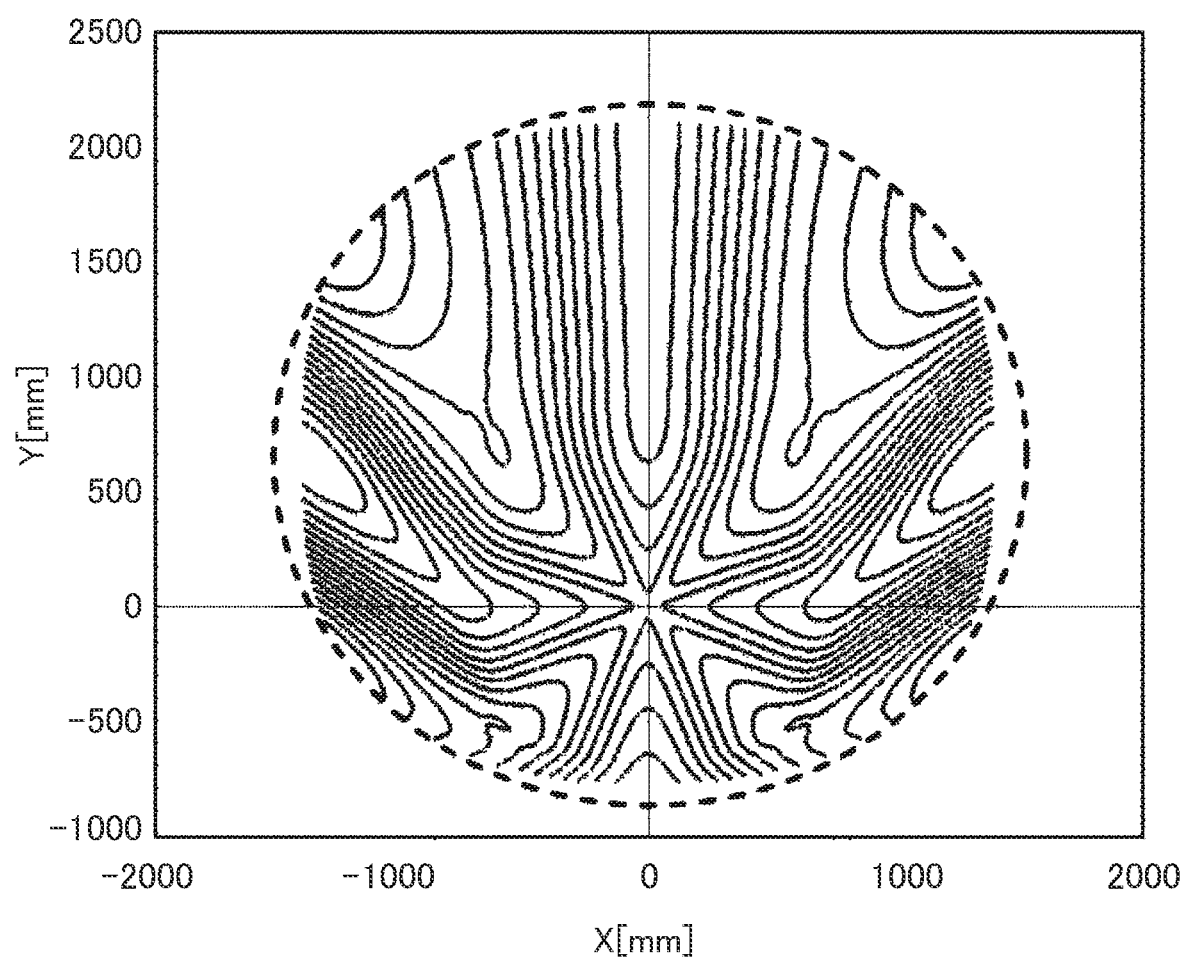
FIG. 5 is the magnetic field distribution in orbit plane in the accelerator 1 in accordance with the embodiment.

For the purpose of producing an orbit configuration and stable betatron oscillations around the orbit as described above, the accelerator 1 in accordance with the embodiment adopts magnetic field distribution in which a minimum and a maximum of the magnetic field emerge four times per circle along the beam orbit. FIG. 4 illustrates magnetic field distributions along an orbit. The magnetic field distribution illustrated in FIG. 4 is along each of orbits of 235-MeV energy, 202-MeV energy, 157-MeV energy, 75.5-MeV energy, and 11.5 MeV-energy, in which the vertical axis represents a magnetic field and the horizontal axis represents a distance in the orbital direction when zero corresponds to the orbit dense region and one corresponds to the orbit sparse region in the downstream half turn. In this manner, while an average magnetic field is increased in terms of energy, the magnetic field distribution providing isochronism and betatron oscillations can be achieved even in eccentric orbital arrangement as in the accelerator by appropriately determining the amplitude. The magnetic field distribution on the center plane is also shown as an isofield contour map. FIG. 5 represents the isofield contours in which the magnetic field on the center plane is divided into 16 stages between the maximum magnetic field 2.54 T and the minimum magnetic field 0.32 T. Similarly to FIG. 3, the origin of the X-Y plane corresponds to the injection point and the Y axis corresponds to the left-right symmetry axis AA' connecting the sparse region and the dense point. The circle shown by the broken line in each of FIGS. 3, 2 and 5 is a circle with a 1526-mm radius, and all the energy orbits are involved inside the circle.

Figure 6:
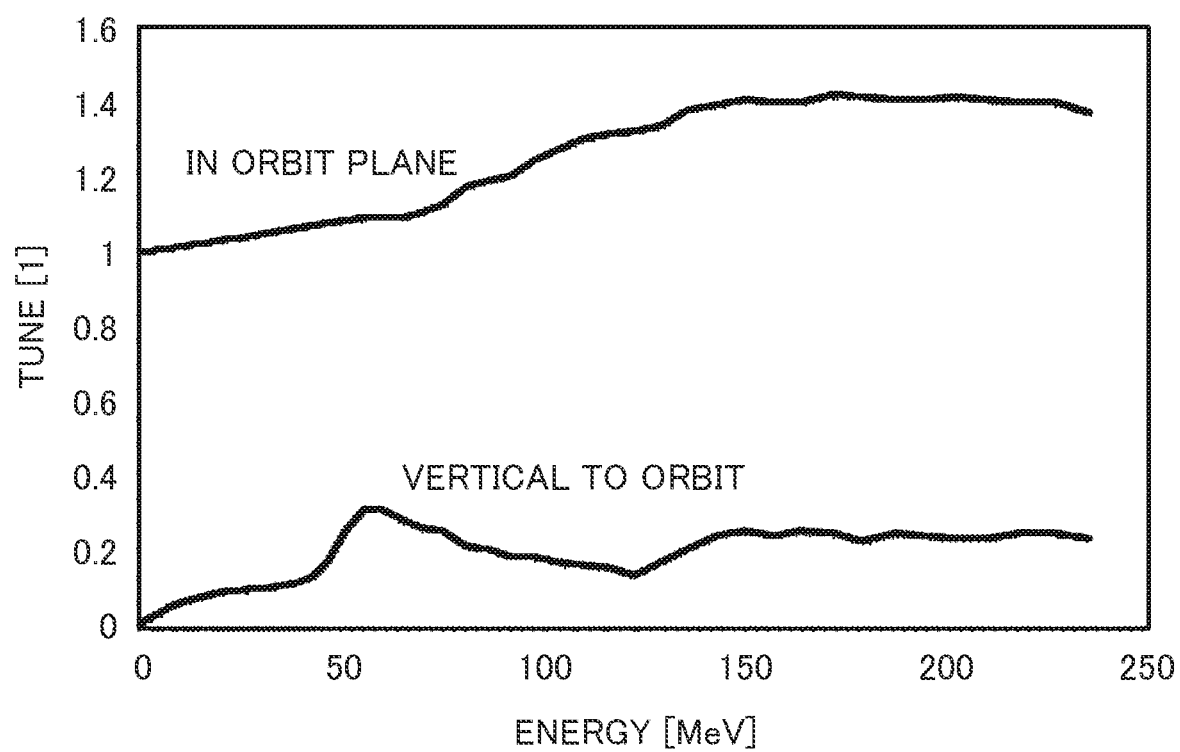
FIG. 6 is a graph illustrating the dependence of a tune on the beam energy of the accelerator 1 in accordance with the embodiment.
Figure 7:
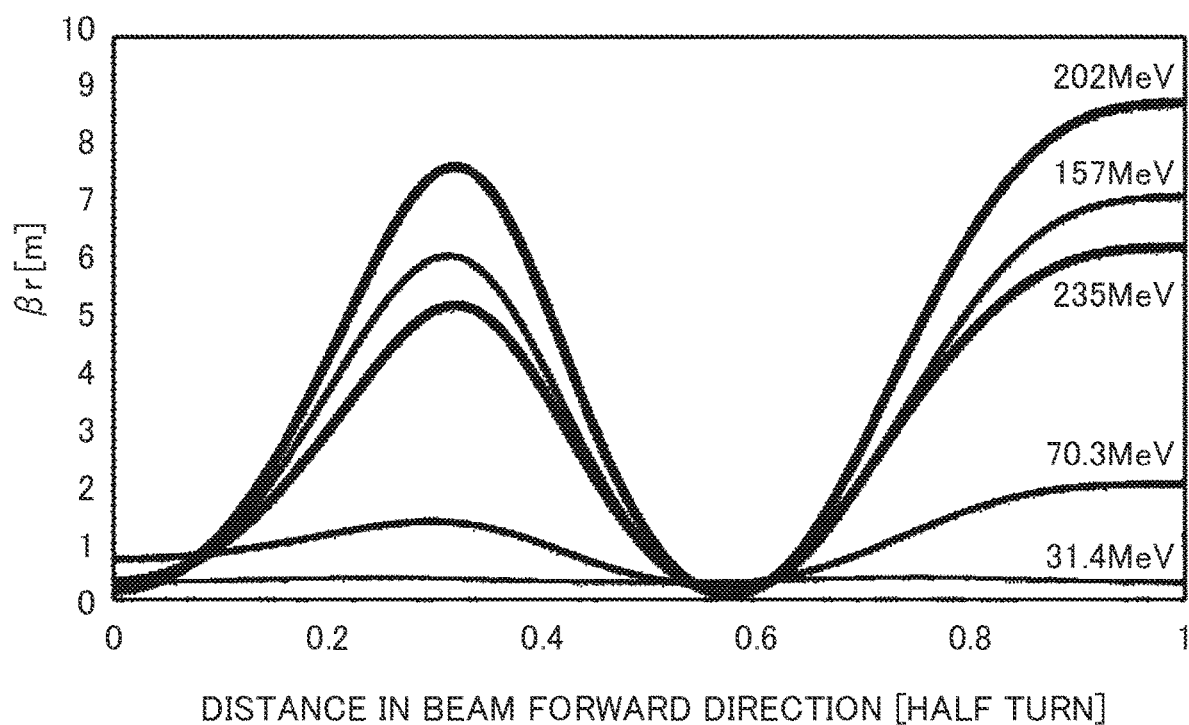
FIG. 7 is a graph illustrating a beta function in an in-pane direction of acceleration in the accelerator 1 in accordance with the embodiment.
Figure 8:
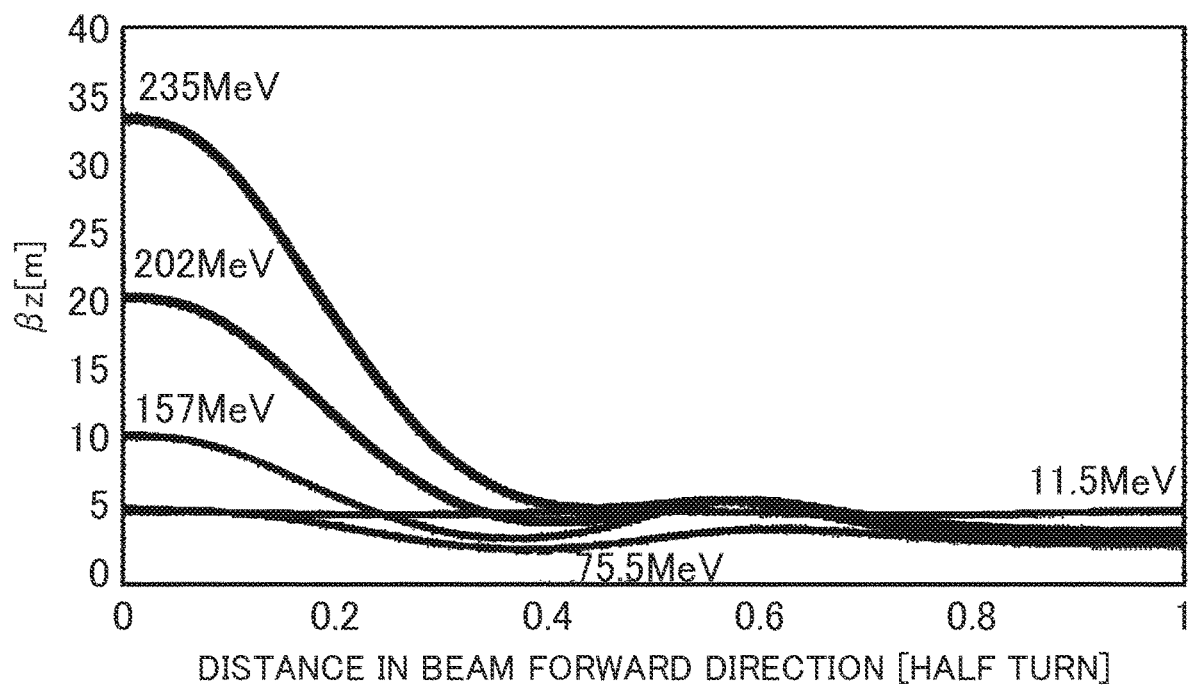
FIG. 8 is a graph illustrating a beta function in a direction vertical to the acceleration plane of the accelerator 1 in accordance with the embodiment.

Under the above conditions, the evaluation results of betatron oscillation frequency (tune) around orbit are shown in FIG. 6. A tune is calculated based on a magnetic field gradient obtained from the on-orbit magnetic field and the subsequent and preceding energy magnetic fields. In the lower energies, the tune in the orbit plane is approximately one, and increases with increasing acceleration. The tune in a direction vertical to the orbit plane is also approximate zero in the lower energies, and a range from zero or higher to lower than 0.5 exists in the full energy regions. A betatron function β corresponding to the betatron oscillation amplitude exists in each of an acceleration in-plane direction (r) and a direction vertical to the acceleration plane (z), and the behavior is illustrated in FIG. 6, FIG. 7. As illustrated in FIG. 6 and FIG. 7, β has a tendency to increase in the z direction as compared with the r direction. For example, in comparison of a maximum value, the β in the r direction takes it in the sparse region and indicates 10 m or less at a maximum. On the other hand, the β in the z direction takes the maximum value in the dense region and has a magnitude of the order to 35 m. A beam size caused by the betatron oscillations is calculated by the square root $\sqrt{(\varepsilon\beta)}$ of the product of emittances ε and β. Then, where the beam having emittances which are equal in value in the r direction and the z direction moves in circle in the accelerator, the beam size in the z direction in the dense region becomes maximum in the orbit. For example, if the emittance is 1 πmm·mrad, the beam size in the z direction in the dense region is the order of 6 mm. Therefore, the need for a reduction of variations in convergent force acting on the beam in the region of the beam size arises in preventing a tune for causing the beam to orbit stably, that is, for the orbiting beam, from deviating greatly from the values shown in FIG. 6. The convergent force for the beam is proportional to the magnetic field gradient in a direction vertical to the beam orbit (a quadrupole magnetic field). The quadrupole magnetic field is oscillatively distributed in a range of ±4 T/m in the magnetic field distribution illustrated in FIG. 5, stable betatron oscillations are provided as a result of being acted upon by convergence/divergence during orbit. Therefore, a change in quadrupole magnetic field caused by the beam size is required to be reduced sufficiently for the on-orbit quadrupole magnetic field. Factors responsible for the change of the quadrupole magnetic field in the finite-size beam include a second derivative of a magnetic field along a direction vertical to the beam orbit, that is, the gradient of magnetic field gradient. The second derivative of the magnetic field along a direction vertical to the beam orbit is referred to as a "sextupole magnetic field", and in the region in which the sextupole magnetic field exists, the convergent force acting on particles forming a beam varies depending on position in the beam, resulting in variations in oscillation frequency between the betatron oscillations of the respective particles. A difference in quadrupole magnetic field inside the beam is proportional to a product of the sextupole magnetic field and the beam size. Further, it is known that the sensitivity of the influence of a change in the quadrupole magnetic field occurring at a certain point of the orbit, on the betatron oscillation frequency is proportional to β at the point. Thus, the variations in betatron oscillations are proportional to the integral of the products of β to the three-halves power (i.e., the cube of the beam size) and the sextupole magnetic field throughout the orbit.

Figure 9:
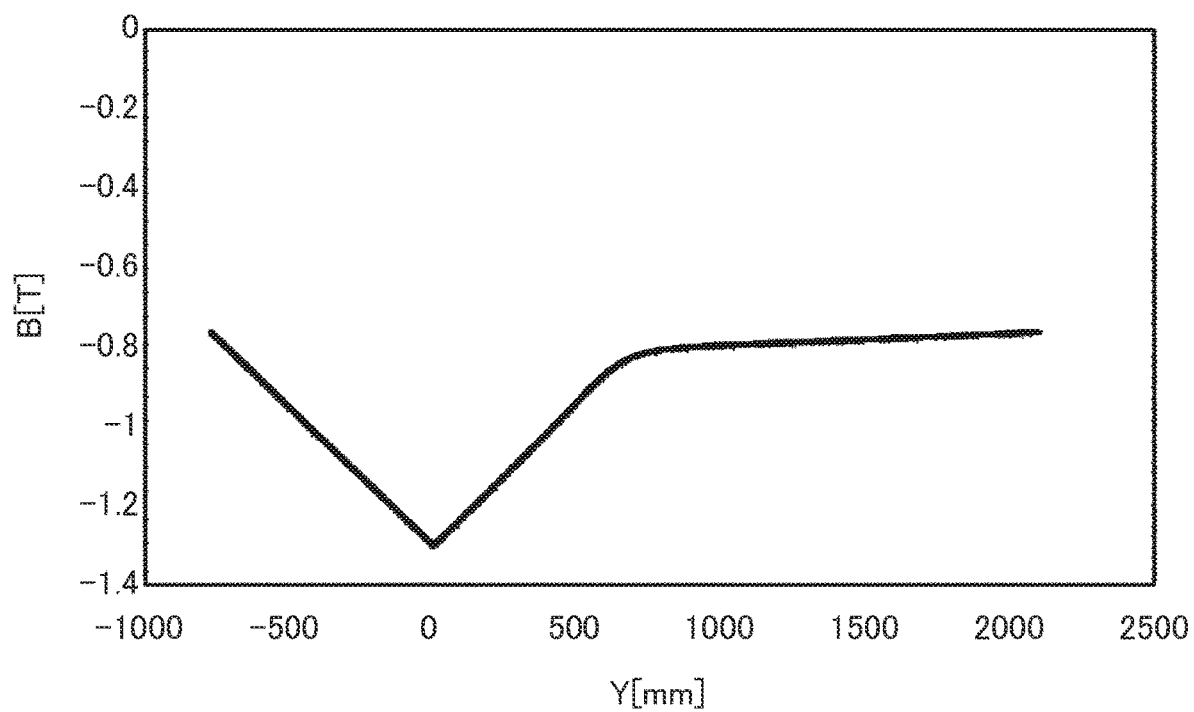
FIG. 9 is a graph illustrating the magnetic field distribution along left-right symmetry axis of the accelerator 1 in accordance with the embodiment.

Based on the above awareness, the present invention constructs the magnetic field distribution to reduce variations in betatron oscillations by focusing on the sextupole magnetic field in the dense region in which the betatron function becomes larger. The magnetic field distribution in accordance with the embodiment has a feature that the magnetic field distribution in the dense region is set as approximately-linear magnetic field distribution with respect to a direction vertical to the beam orbit (direction parallel to the Y axis). Specifically, on the left-right symmetry axis AA' of the accelerator 1, the magnetic field takes a shape capable of being approximated by use of a linear function on the dense point side as illustrated in FIG. 9. In other words, the magnetic field distribution is designed such that occurrence of a second derivative of the magnetic field along two in-plane directions vertical to the beam orbit (gradient of magnetic field gradient) is inhibited. Specifically, in the distribution, the magnitude of the magnetic field is monotonously decreased on the magnetic field gradient −0.7 T/m from a magnetic field −1.3 T at the injection point (Y=0 mm) to the outermost contour of the dense region in the orbit radial direction. In such a magnetic field, the magnetic field distribution causes the sextupole magnetic field and higher-order multipole magnetic fields to be zero, resulting in no occurrence of variations in convergent force in the beam.

Figure 10:
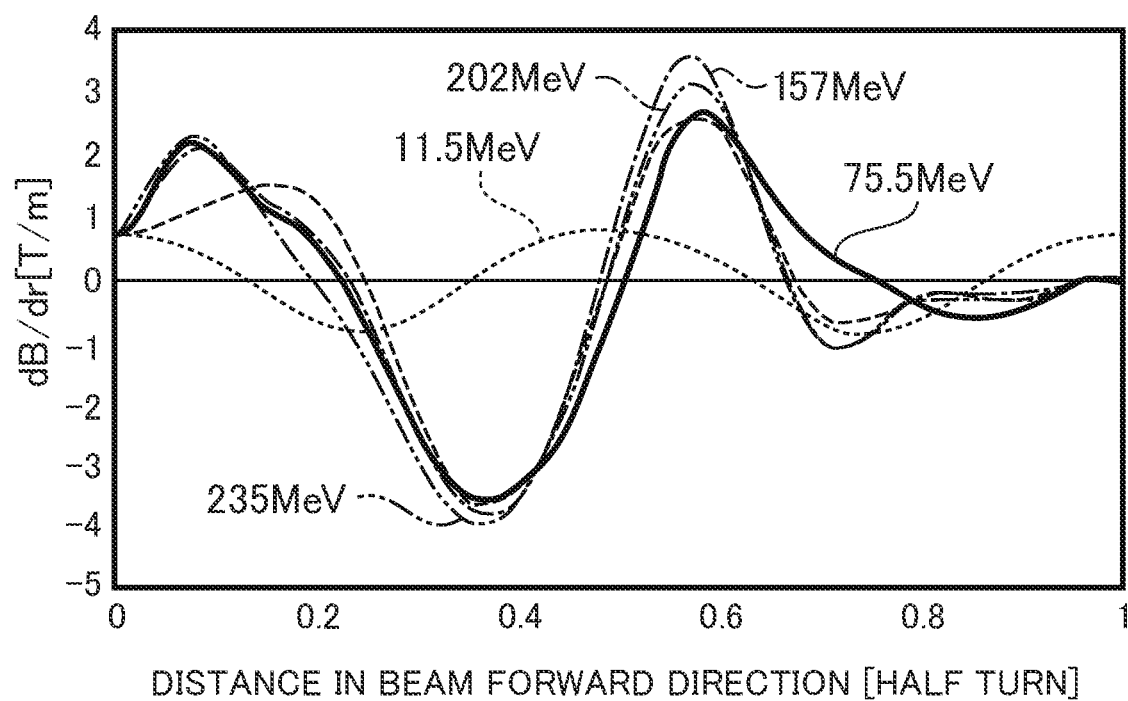
FIG. 10 is a graph illustrating the quadrupole magnetic field distribution along the orbit in the accelerator 1 in accordance with the embodiment.
Figure 11:
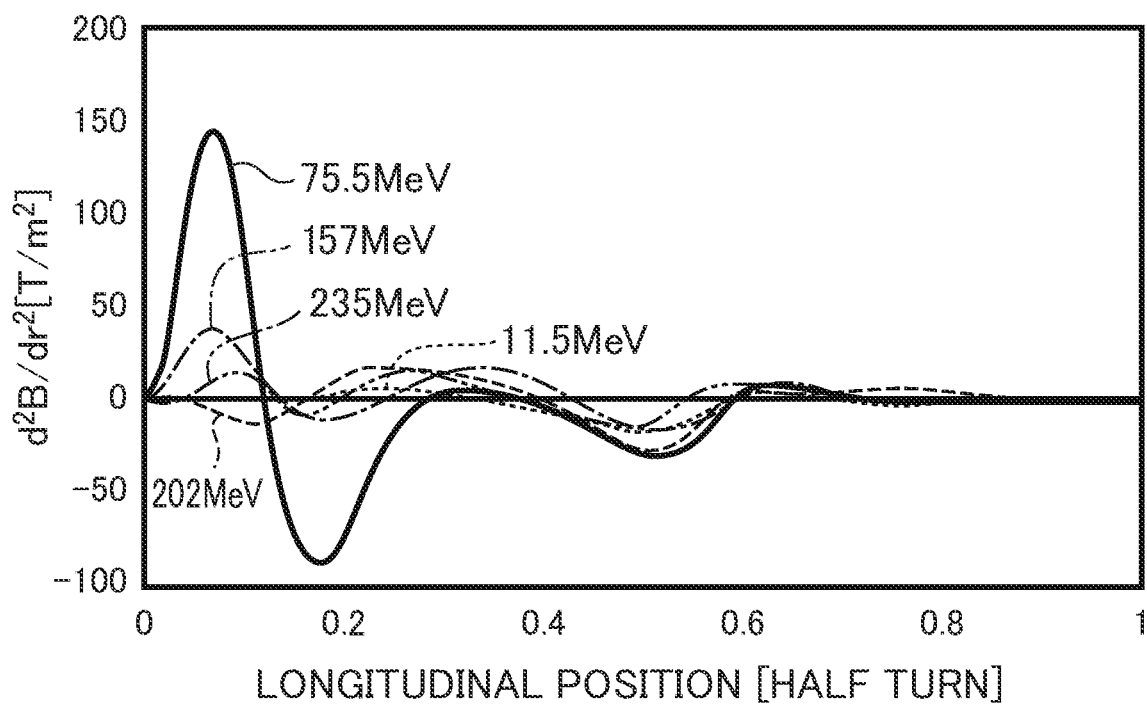
FIG. 11 is a graph illustrating the sextupole magnetic field distribution along the orbit in the accelerator 1 in accordance with the embodiment.

To verify this, FIGS. 10, 11 illustrate values of the quadrupole magnetic field and the sextupole magnetic field along the orbit. As illustrated in FIG. 10, the quadrupole magnetic field alternately transitions to the positive region and to the negative region along the beam orbit. When the quadrupole magnetic field is in the positive region, the convergent force in the z direction is imposed, and when it is in the negative region, the convergent force in the r direction is imposed. Therefore, as a whole, a stable orbital movement is provided in the r direction and also in the z direction. Further, as illustrated in FIG. 11, the sextupole magnetic field is zero in the dense region (a region where the horizontal axis is zero). This enables stability of a finite-size beam. For example, in a variable energy accelerator to which the present invention is not applied, a sextupole magnetic field of the order of 100 T/m2 may occur in the dense region. In this case, a quadrupole magnetic field deviation of ±0.6 T/m occurs in a region of 6 mm corresponding to a beam size. Then, because of occurrence of variations comparable to those in the quadrupole magnetic field 0.7 T/m at the dense point, a convergent force in conformance with design cannot be obtained. Thus, the main magnetic field distribution according to the present invention enables contribution to beam stability and therefore an increase of the amount of current of an orbiting beam.

Figure 12:
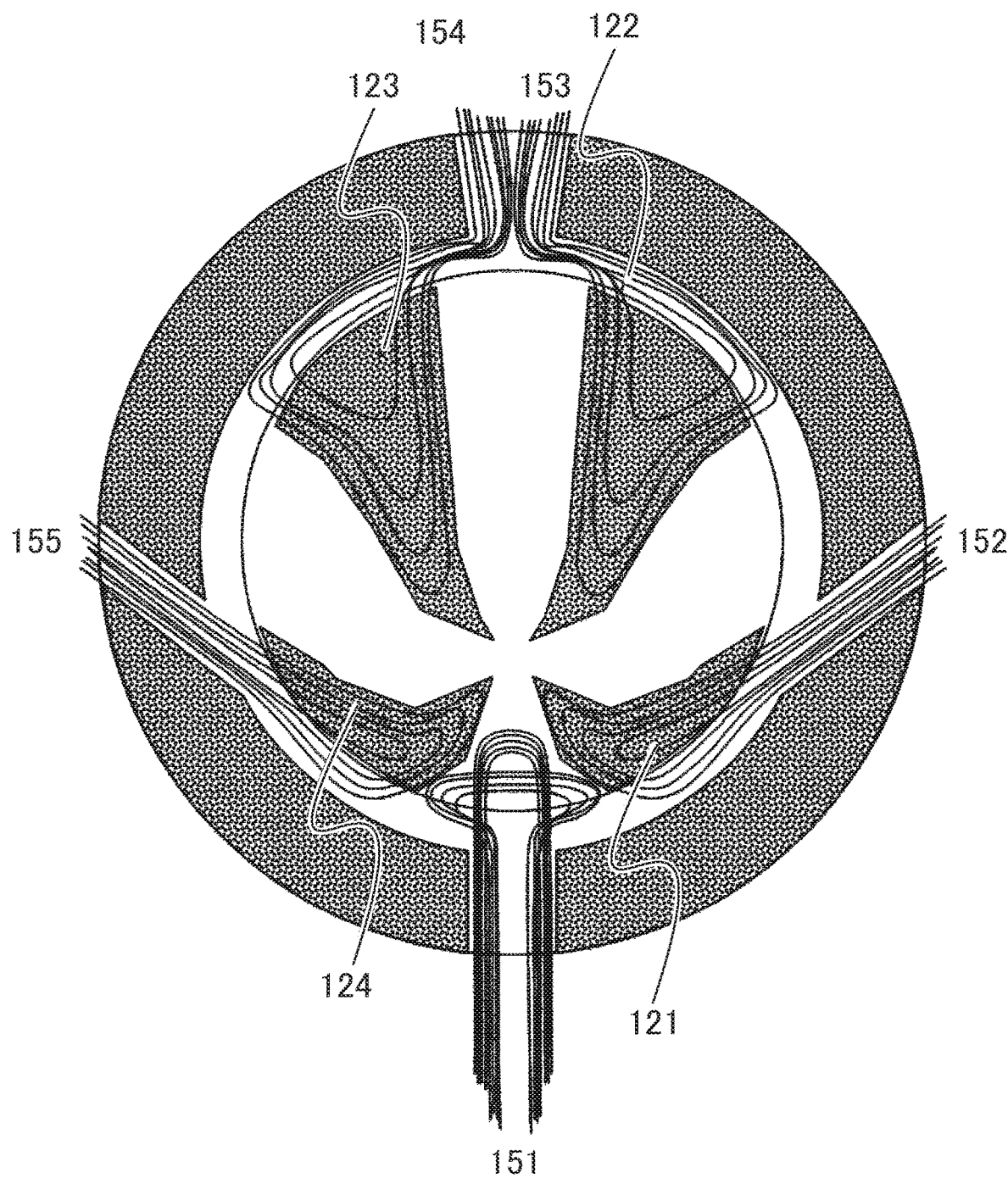
FIG. 12 is a diagram illustrating trim coil placement of the accelerator 1 in accordance with the embodiment.

In the accelerator 1 in accordance with the embodiment, a trim coil attached to the electromagnet 11 is used to excite the magnetic field distribution shown in FIG. 5. FIG. 12 illustrates a shape of the trim coil. Trim coils 151 to 155 are installed in magnetic pole projections 121 to 124 and the dense region. Each trim coil has a plurality of systems in which the amount of excitation can be independently adjusted. The trim coil is a coil for correcting the magnetic field placed in a region at a distance in the z direction from the plane in which the beam orbits. The accelerator 1 includes the trim coils 152 to 155 for adjustment to magnetic field distribution placed in the magnetic pole projections. The trim coils 152 to 155 are connected to a power supply, and from the results of magnetic field measurements separately obtained, the results of beam monitor measurements, and/or the results of magnetic field measurements, the amount of excitation is controlled such that a predetermined magnetic field distribution is approached. Further, a trim coil 151 for dense region is separately provided for obtaining a linear magnetic field distribution in the dense region, which is a feature of the embodiment. Similarly to the trim coils 152 to 155, for the trim coil 151 the amount of excitation is also adjusted in order to adjust the magnetic field in the dense region from the results of magnetic field measurements and/or the results of measurements of the amount of orbiting beams.

Specifically, the trim coil is adjusted such that the change in quadrupole magnetic field caused by the beam size is reduced sufficiently for the quadrupole magnetic field in the dense region (magnetic field gradient), as described above. A change in quadrupole magnetic field inside the beam is proportional to the product of the sextupole magnetic field (gradient of magnetic field gradient) and the beam size, and also an expansion of the betatron oscillation frequency inside the beam is proportional to the integral of the products of the sextupole magnetic field and the cube of the beam size throughout the orbit. Therefore, the greatest effect of stably moving beams in orbit is produced by setting the trim coil such that, in the dense point where the beam size in the z direction is maximum, the product of the gradient of magnetic field gradient and the beam size of the beam passing through the dense region becomes smaller than the magnetic field gradient. As a result, the variable energy accelerator expected to increase the amount of beams can be achieved.

LIST OF REFERENCE SIGNS

1 . . . Accelerator
11 . . . Magnet
12 . . . Ion source
13 . . . Coil
14 . . . Return yoke
20 . . . Interior space
31, 32 . . . Radiofrequency cavity
40 . . . Extraction septum electromagnet
50 . . . Massless septum coil
111 . . . Beam extraction through hole
112, 113 . . . Coil connection through hole
114 . . . Through hole for incoming radiofrequency
115 . . . Beam injection through hole
121 to 124 . . . Magnetic pole projection
130 . . . Injection point
140 . . . Beam extraction channel
151 to 155 . . . Trim coil

The invention claimed is:

1. An accelerator, comprising:
   a dense region in which orbits of different energies densely gather as a result of using a radiofrequency electric field to accelerate an ion orbiting in an isochronous magnetic field in order to cause a beam orbit to be displaced in a specific direction with increasing acceleration; and
   a sparse region in which orbits of different energies are sparsely discrete from one another,
   wherein the magnetic field has a magnetic field gradient in a radial direction of a beam orbit in the dense region, and a product of a gradient of magnetic field gradient and a beam size passing through the dense region becomes smaller than the magnetic field gradient.

2. The accelerator according to claim 1,
   wherein the magnetic field gradient in the radial direction in the dense region is approximately linear.

3. The accelerator according to claim 1,
   wherein a sextupole magnetic field in the dense region is zero.

4. An accelerator, comprising:
   a pair of magnets that are placed facing each other to create a magnetic field between them; and
   a radiofrequency cavity in which ion beams are accelerated,
   wherein the magnets create a magnetic field such that a plurality of beam closed orbits of a ring shape on which the ion beams of different energies respectively orbit and the closed orbits densely gather on one side,
   the magnetic field created by the magnets has a magnetic field gradient in a radial direction of the closed orbits, and
   in the magnetic field created by the magnets, a product of a gradient of the magnetic field gradient and a size of the ion beam becomes smaller than the magnetic field gradient.

5. The accelerator according to claim 4,
   wherein the magnetic field created by the magnets has the magnetic field gradient in the radial direction of a region in which the closed orbits densely gather, the magnetic field being approximately linear.

6. The accelerator according to claim 4, further comprising:
   a trim coil for a dense region that is placed in a region in which the closed orbits densely gather.

* * * * *